United States Patent [19]

Ishihara et al.

[11] 4,243,661
[45] Jan. 6, 1981

[54] GROWTH INCREASING AGENTS

[75] Inventors: Eisuke Ishihara, Miyanonishi; Hiroshi Yonehara, Tokyo; Katsuyuki Akasaki, Shimizu; Masao Minowa; Katsumi Kobayashi, both of Shizuoka, all of Japan

[73] Assignee: Kumiai Chemical Industry Co., Ltd., Tokyo, Japan

[21] Appl. No.: 32,253

[22] Filed: Apr. 23, 1979

Related U.S. Application Data

[63] Continuation of Ser. No. 830,773, Sep. 6, 1977, abandoned, which is a continuation of Ser. No. 736,523, Oct. 28, 1976, abandoned, which is a continuation of Ser. No. 681,198, Apr. 28, 1976, abandoned.

[30] Foreign Application Priority Data

Oct. 28, 1975 [JP] Japan .............................. 50-128910

[51] Int. Cl.³ .......................................... A61K 35/00
[52] U.S. Cl. .................................................. 424/117
[58] Field of Search ........................................ 424/117

[56] References Cited

U.S. PATENT DOCUMENTS 3,790,668  2/1974  Raun .................................... 424/117

FOREIGN PATENT DOCUMENTS 2507565  8/1975  Fed. Rep. of Germany ........... 424/117
48-19432  6/1973  Japan .................................... 424/117

OTHER PUBLICATIONS

*Journal of Antibiotic,* vol. XXIII, No. 5, 1970.

*Primary Examiner*—Frederick E. Waddell
*Attorney, Agent, or Firm*—Stevens, Davis, Miller & Mosher

[57] ABSTRACT

The present invention relates to a veterinary medicine containing multhiomycin as an effective ingredient and provides a medicine for promoting growth of animals including birds, fishes and shellfishes and preventing various kinds of diseases of animals or fishes and shellfishes which contains multhiomycin as an essential component.

6 Claims, 2 Drawing Figures

GROWTH INCREASING AGENTS

This is a continuation of application Ser. No. 830,773 filed Sept. 6, 1977 which in turn is a continuation of Ser. No. 736,523 filed Oct. 28, 1976 which in turn is a continuation in part of application Ser. No. 681,198 filed Apr. 28, 1976, all now abandoned.

BACKGROUND OF THE INVENTION

1. Field of the Invention

The present invention relates to a veterinary medicine containing multhiomycin as an effective ingredient. More particularly, this invention provides a medicine for promoting growth of animals and preventing various kinds of diseases of animals which contain multhiomycin as an essential component.

2. Description of the Prior Art

The present inventors have pursued extensive studies on various kinds of antibiotics produced by microorganisms and continued further study on multhiomycin, an antibiotic disclosed in the Journal of Antibiotics Vol. XXIII, No. 5, pp. 231–237 (1970) by H. Yonehara (one of the present inventors) et al.

H. Yonehara et al. reported in the said publication that multhiomycin is a new antibiotic obtained from the micelium of Streptomyces SP 8446-CCI, which is extracted with methanol and purified by silica gel chromatography and forms yellow needle-shaped crystals, melts at above 300° C. and has no or negligible optical activity. $C_{44}H_{45}O_{11}N_{11}S_5$ was suggested for its molecular formula by elemental analysis and molecular weight determination and it was further found to exhibit inhibitory activity against gram-positive bacteria but no activity against gram-negative bacteria, mycobacteria and fungi. However, the above authors did not find that multhiomycin is useful as veterinary medicine.

SUMMARY OF THE INVENTION

The inventors continued an extensive study on multhiomycin and the use thereof and through their continued studies accomplished the present invention.

The object of the present invention is to provide a veterinary medicine containing multhiomycin as an essential component.

DESCRIPTION OF THE PREFERRED EMBODIMENTS

Figure 1:
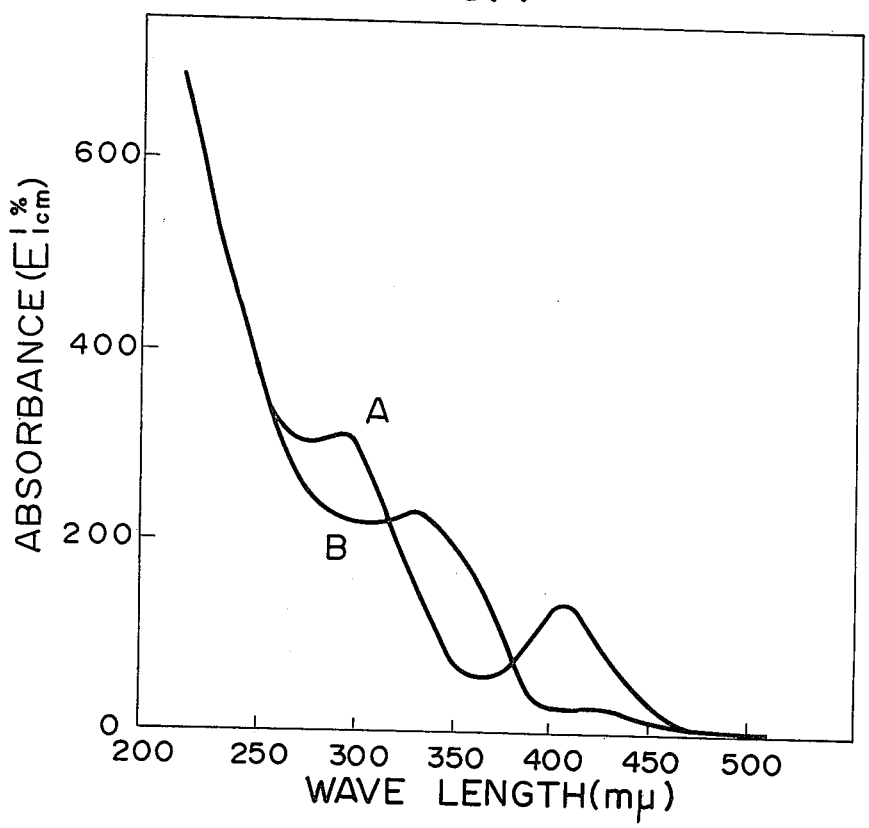
FIG. 1 is a graph showing the ultraviolet adsorption curves of multhiomycin in alkaline methanol (A) and in neutral or acid methanol (B)

*Streptomyces* sp. 8446-CCI used in the present invention has the following morphological cultural physiological characteristics.

Cultural characteristics of *Streptomyces* sp. 8446-CCl in various culture medium

| Medium | Cultural characteristics |
| --- | --- |
| Sucrose nitrate agar | G: thin, colorless to yellowish gray<br>AM: abundant, powdery, white<br>SP: very slight, yellowish gray |
| Glycerol-nitrate agar | G: thin, colorless to yellowish gray<br>AM: poor, powdery, white<br>SP: very slight, yellowish gray |
| Glucose-asparagine agar | G: moderate, yellowish gray with pale yellowish brown reverse<br>AM: abundant, velvety, light gray to light brownish gray<br>SP: slight, pale yellowish brown |
| Glycerol-calcium malate agar | G: moderate, spreading and penetrating into agar, yellowish gray<br>AM: abundant, velvety, light brownish gray with whitish patch<br>SP: very slight, yellowish gray |
| Starch agar | G: moderate, spreading and penetrating into agar, yellowish gray with light brownish gray reverse<br>AM: abundant, velvety, light gray with brownish tinge<br>SP: very slight, yellowish gray |
| Peptone beef extract agar | G: moderate, pale yellowish brown with yellowish brown reverse<br>AM: poor, powdery, white at margin of colony<br>SP: yellowish brown |
| Glucose peptone-beef-extract agar | G: thick and wrinkled, yellowish gray<br>AM: poor, powdery, white at margin of colony<br>SP: yellowish brown |
| Glucose peptone agar | G: thin, pale yellow<br>AM: none<br>SP: slight, pale yellow |
| Glucose casein digest-yeast-beef agar | G: moderate and wrinkled, pale yellowish brown reverse<br>AM: moderate, velvety, light gray with brownish tinge<br>SP: slight, pale yellowish brown |
| Oatmeal-yeast extract agar | G: moderate, spreading and penetrating into agar, yellowish gray<br>AM: abundant, velvety, light gray with brownish tinge<br>SP: very slight, yellowish<br>G: thick and wrinkled |
| Potato plug | AM: abundant, light gray with brownish tinge<br>SP: dark brown |
| LOEFFLER'S blood serum | G: moderate, dark brown<br>AM: poor, powdery, white<br>SP: dark brown<br>G: surface ring, pale yellowish brown |
| Gelatin | AM: none<br>SP: brown<br>G: surface ring, pale yellowish brown |
| Milk | AM: abundant, powdery white<br>SP: brown to dark brown<br>G: thin, colorless |
| Cellulose | AM: abundant, powdery, light gray<br>SP: none<br>G: moderate, yellowish gray to pale yellow |
| Glycerin-asparagin | AM: abundant, powdery brownwhite to light brown gray<br>SP: very slight, yellowish gray<br>G: moderate, grayish yellow brown |
| Thyrosine agar | AM: moderate, powdery white<br>SP: dark yellow brown<br>G: thick, pale yellow brown to grayish yellowish brown |
| Yeast-malt agar | AM: abundant, velvety, light brownish gray<br>SP: pale yellow brown<br>G: thin, yellowish gray |
| Oatmeal agar | AM: abundant, velvety, light brownish gray<br>SP: slight, yellowish gray |

G: Growth
AM: Aerial mycelium
SP: Soluble pigments

In the table above, color was determined by the method described in "Color Harmony Manual" published by Container Corporation of America.

Physiological Properties:

Optimum growth condition:pH 7.0-aerobic

Growth condition:pH 6.2-7.8 ungrowable under 5° C. and above 45° C. and ungrowable under anaerobic condition (ungrowable in a lower layer in the case of stab culture in a thick yeast-melt agar culture medium)

Color production:prepare deep brown color in a natural culture medium and melamine color in tyrosine culture medium Hydrogenation of starch:Liquefy Decomposition of cellulose:no decomposition Reduction of nitrate:reduct Decomposing powder of protein:gelation liquefication milk peptonization, blood serum liquefaction Utilization of hydrocarbons:utilizes as carbon source glucose, rhamnose, mannose, milk sugar, raffinose, mannitol, sucrose, glycerin and salicin, and does not utilize arabinose, fructose and cellulose.

Cultural and physiological characteristics of the strain 8446-CCI are as shown in the above. The strain was determined to belong to "Gray series" of "TRESER and BACKUS" by the fact that the color of aerial mycelium was light gray to light brownish gray. The substrate mycelium or reverse side of colony showed no distinctive colors (yellowish gray to yellowish brown) on all media. Soluble pigments were produced slightly and no distinctively (yellowish gray to pale yellowish brown) on synthetic or some organic media. Chromogenic pigments (yellowish brown to dark brown) were produced on most organic media and melanoid pigment on tyrosine agar.

Judging from the above-described morphological culture physiological characteristics, Streptomyces sp. 8446-CCI is considered to be a strain belonging to Streptomyces antibioticus. This strain was deposited in an unrestricted form with the Fermentation Research Institute of Agency of Industrial Science and Technology of Japan (No. 8-15-chome Higashi Inage, Chiba-city, Chiba Prefecture, Japan) under Strain Deposit No. PERM-P 3,284 and the samples of the strain can be issued to the third parties after the Japanese Patent Application No. 128910/1975 which is the base application of this application, is open.

For obtaining multhiomycin, a multhiomycin-producing strain belonging to genus Steptomyces is cultured in a culture medium which comprises a carbon source and a nitrogen source. If necessary, it is also possible to add to the culture medium sodium chloride, phosphate or a very small amount of metal ions. A culture medium which contain dextrine, dry yeast, methionine, sodium chloride and calcium carbonate, and which contain starch, cotton-seed flour, methionine, sodium chloride and calcium carbonate are best suited for production of multhiomycin.

Although cultivation of the multhiomycin-producing strain can be accomplished by solid culture, it is more advantageous to employ liquid culture, particularly submerged culture, for mass cultivation. Cultivation can be conducted under an aerobic or semi-aerobic condition. For instance, it is possible to carry out cultivation under flow of germ-free air or by surface culture with no aeration. Cultivation temperature is usually within the range of 10° to 50° C. preferably 23° to 32° C., but in most cases a temperature of around 27° C. is found to be optimal.

Generally, production of multhiomycin reaches its maximum after about 1 to 9 days cultivation in the case of shaking culture and in about 1 to 8 days cultivation in the case of aerated tank culture.

The collection of multhiomycin can be accomplished by any suitable known methods generally used in separating and collecting the antibiotics from a culture of microorganisms or by combining such methods.

Now the methods of cultivation as well as the methods for collecting multhiomycin are described by way of example.

EXAMPLE 1

Cultivation of Multhiomycin

A seed culture solution of Streptomyces sp. 8446-CCI strain was inoculated in 30 liter of culture medium (with adjusted pH of 5.6) containing 2.5% of dextrine, 2.0% of dry yeast, 0.5% of sodium chloride and 0.4% of calcium carbonate. The culture medium was subjected to culturing under agitation by agitator and under aeration with 15 liter/min. of air.

As the production of multhiomycin reached its maximum level after 96 hours cultivation, the cultivation was suspended at that point and the myceline were filtered out to obtain about 10 kg of wet mycelium. These mycelium were extracted first with 15 liter of methanol and then with 15 liter of a mixed solvent of acetone and methanol mixed in the mixing ratio of 4:1 in volume and then the two extracted solutions were combined and subjected to vacuum distillation (at 60° C.) to separate methanol and acetone from the mixed solution, and 500 ml of remaining aqueous solution was further extracted with 1 liter of mixed solvent of isopropanol and dichloroethane mixed in the ratio of 1:4 in volume, isopropanol and dichloroethane were distilled off under vacuum (at 60° C.) from this isopropanol-dichloroethane mixed extracted solution and the residual oily substance was dissolved in a mixed solvent of isopropanol and dichloroethane (mixed in the ratio of 1:4 in volume), and to this solution was added portionwise, n-hexane in amount 1.5 times as much as that of the solution, whereby yellow sediment of multhiomycin was obtained. This sediment was collected on a glass filter and washed once with 10 ml of methanol, obtaining 6.2 gr of crude crystals of multhiomycin (with a purity of 90% ).

1 gr. of these crude crystals of multhiomycin was dissolved in 800 ml of ethyl acetate containing 10% of DMF and then allowed to stand at room temperature (about 20° C.) for two days, consequently obtaining 660 mg of needle crystals of multhiomycin (with a purity of 100%).

The antibiotic multhiomycin obtained has the following physicochemical properties.

The elemental analysis of multhiomycin showed the following constituents: C 49.74; H 4.17; O 16.74; N 15.13; and S 15.03, and molecular weight measured by the vapor pressure method was 1064. It is anticipated from these facts that multhiomycin has the molecular formula, $C_{44}H_{45}O_{11}N_{11}S_5$. Melting point (decomposition point) of this antibiotic is higher than 300° C.

Figure 2:
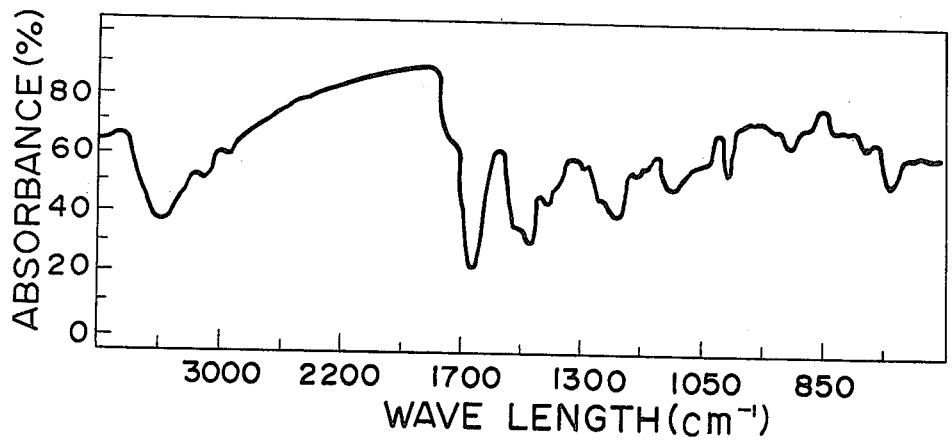
FIG. 2 shows an infrared adsorption curve of the multhiomycin as measured in the form of a potassium bromide tablet.

The ultraviolet absorption curve of multhiomycin is as shown in the graph of FIG. 1. As seen from the graph, it shows the maximum absorptivity at 328 m$\mu$ ($E_{1cm}^{1\%}$ 220) and 420 m$\mu$ ($E_{1cm}^{1\%}$ 20) in the neutral or acid methanol (B), while in the alkaline methanol (A) it shows the maximum absorptivity at 292 m$\mu$ ($E_{1cm}^{1\%}$ 255) and 406 m$\mu$ ($E_{1cm}^{1\%}$ 132). FIG. 2 shows the infrared absorption curve of multhiomycin (in potassium bromide tablet), from which is will be seen that high absorptivity is observed at 3380 cm$^{-1}$, 1660 cm$^{-1}$, 1520 cm$^{-1}$, 1470 cm$^{-1}$, 1200 cm$^{-1}$, 1110 cm$^{-1}$, 1015 cm$^{-1}$, 910 cm$^{-1}$ and 750 cm$^{-1}$.

Multhiomycin is soluble in dimethylformamide, dimethyl sulfoxide and pyridine, but is only slightly soluble in ethyl acetate, methanol, ethanol and dioxane and is insoluble in water, acetic acid, n-hexane, ether, chloroform and many other organic solvents.

As for color reaction of multhiomycin, it develops various colors by the ferric chloride reagent, Folin's reagent and Lemieux reagent, but it develops no color by the ninhydrin reagent, Fehling's reagent and Ponceau-3R reagent or in the buret reactions.

Multhiomycin remains stable, when heated in an aqueous solution at 100° C. at a pH of 2 to 5 for five minutes. It is a slightly acidic and is in the form of yellow needle crystal. No optional activity is observed in its 1% solution.

As a medicine for animals using multhiomycin, the fungus containing multhiomycin obtained by the cultivation of Streptomyces sp. 8446-CCI, or multhiomycin producing fungus, crude multhiomycin or refined multhiomycin can be directly administrated to the animals or fishes and shellfishes in the form of a solution, emulsion, suspension, wettable powder, dust, tablets or injection, or administrated to the animals or fishes and shellfishes by adding to their feed or drinking water. Multhiomycin can also be used as a growth stimulator for a wide variety of animals including bird, fishes and shellfishes, for example poultry such as laying hens, broilers, turkeys, ducks, etc., livestock such as cattle, horses, pigs, sheeps, goats, mink, etc., pet animals such as dogs, cats, pigeons, etc., or laboratory animals such as mice, rats, rabbits, etc., or fishes and shellfishes such as carp, trouts, eels, goldfishes, sweetfishes, sea gold breams, yellowtails, oysters, scallops, etc.

In administering multhiomycin to said animals, or fishes and shellfishes, it may be directly blended in feed or drinking water. More effectively, multhiomycin is once formed into a solution or emulsion or into a wettable powder or suspension and then added to feed or drinking water given to the animals including birds, fishes and shellfishes. In case of using multhiomycin in the form of solids such as wettable powder or suspension, good results can be obtained if the particle size of multhiomycin is within the range of 1 to 100µ, preferably less than 5µ. This is due to the property of multhiomycin of not being absorbed in the body of the animal or fish and shellfish to which it is administered.

Further multhiomycin can be given directly to animals, fishes and shellfishes as growth promoting agent in a form of powder, grain, tablet or suspension without mixing with feed or drinking water.

As for the optimal dosage of multhiomycin for animals including birds, fishes and shellfishes, it is usually given in an amount of 0.1 to 500 ppm, preferably 0.5 to 100 ppm, by blending it in feed or drinking water, although the amount is somewhat varied depending upon the degree of growth of the object animals including birds, fishes and shellfishes. This level of concentration is far lower than dosage required for various kinds of diseases of animals including birds, fishes and shellfishes.

In case of using multhiomycin in mixture (blend) with feedstuff, multhiomycin or its mixture (pre-mix) with an extender or diluent such as starch, dextrose, dextrine, calcium carbonate, kaolin or the like is crushed by a crushing machine such as jet pulverizer to prepare a dust, wettable powder or suspension, then this is diluted with a suitable amount of water and adsorbed or spread in a feedstuff such as soybean meal or fish meal to make a feed containing about 0.5 to 10% of multhiomycin, and then this is further blended with feedstuff so that multhiomycin has the prescribed concentration therein. In case that multhiomycin is in the form of a solution or emulsion, it is adsorbed or spread in a feedstuff directly or after diluting it with water to prepare a feed containing about 0.5 to 10% of multhiomycin, and then this is blended with feedstuff in such an amount as to provide a predetermined concentration.

Multhiomycin can be added to any type of feedstuff generally used for animals including birds, fishes and shellfishes such as corn, milo, soybean meal, soybean flour, lucern meal, fish meal, rice bran, wheat flour, wheat bran, fats, cottonseed meal, etc. It is also possible to blend other additives therewith, for example a surfactant or adjuvants such as sodium asparaginate, sorbitan monostearate, sorbitan monolaurate, Tween, calcium carbonate, sodium chloride, choline chloride, vitamines, calcium pantothenate, nicotinic acid amide, folic acid, iron sulfate, magnesium sulfate, zinc sulfate, cobalt sulfate, amino acids, etc., or other feed additives such as sulfa drugs, various kinds of coccidiostats, and other antibiotics and antiparasitics.

Multhiomycin is efficacious not only for promoting growth of animals including birds, fishes and shellfishes but also for improving feed efficiency, egg-laying and fertilization rates as well as for preventing diarrhea (watery feces) of fowls.

Now the physiological effects of multhiomycin are described in detail in the results of tests on promotion of growth of animals including birds, fishes and shellfishes and other matters.

EXAMPLE 2

500 broiler chickens (250 males and 250 females) one-day old after hatching were divided into five groups each of which consisted of 100 chickens (with the same number of males and females) and these groups of chickens were fed with the feeds containing multhiomycin of 0.5, 1, 2 and 4 ppm, respectively, with the control group being fed with feeds to which no multhiomycin was added and such feeding was continued for eight weeks according to a floor pen system.

The results of the test are shown in Table 1 below, from which it is noted that the average body weight of the 8-weeks old chickens in the multhiomycin-added feed groups is higher by 6.4 to 9.0% than that of the counterparts in the control group, while the feed efficiency is improved by an amount of 0.13 to 0.24 over the control.

TABLE 1

| Group | Change of average body weight and feed efficiency | | | | | |
|---|---|---|---|---|---|---|
| | 0-week old | 2-week old | 4-week old | 6-week old | 8-week old | Feed efficiency |
| control | 43 | 245 | 685 | 1330 | 1825 | 2.44 |
| 0.5 ppm | 43 | 245 | 706 | 1412 | 1942 | 2.31 |
| 1.0 ppm | 43 | 247 | 719 | 1419 | 1951 | 2.30 |
| 2.0 ppm | 43 | 250 | 723 | 1423 | 1962 | 2.25 |

TABLE 1-continued

Change of average body weight and feed efficiency

| Group | 0-week old | 2-week old | 4-week old | 6-week old | 8-week old | Feed efficiency |
|---|---|---|---|---|---|---|
| 4.0 ppm | 43 | 247 | 726 | 1431 | 1989 | 2.20 |

(NOTES)
(1) Each numerical value in the table is a mean value (gr).
(2) Feed efficiency = total amount of feed ingested during the entire test period ÷ body weight gain during the entire test period.

Composition of basal feed:
(1) Starter feeds (used in 0 to 4-week period)

| | |
|---|---|
| Corn | 49.5% |
| Soybean meal | 24.5 |
| Milo | 12.2% |
| Lucerne meal | 4.0 |
| Fish meal | 6.5 |
| Sodium chloride | 0.3 |
| Calcium carbonate | 1.5 |
| Calcium phosphate | 1.0 |
| Premix (*) | 0.5 |

125 ppm of Amprolium plus** (Trade mark) was added as a coccidiosis preventive.

(2) Finisher feeds (used in 5 to 8-week period)

| | |
|---|---|
| Corn | 52.0% |
| Soybean meal | 10.0 |
| Milo | 14.5 |
| Fish meal | 9.8 |
| Fats | 7.0 |
| Lucerne meal | 3.5 |
| Sodium chloride | 0.2 |
| Calcium carbonate | 1.5 |
| Calcium phosphate | 1.0 |
| Premix (*) | 0.5 |

125 ppm Amprolium plus** (Trade mark) was added as a coccidiosis preventive.
(*) Premix contains vitamin A, vitamin $D_3$, vitamin E, vitamin $B_1$, vitamin $B_2$, vitamin $B_6$, vitamin $B_{12}$, pantothenic acid, nicotinic acid, choline chloride, folic acid, iron sulfate, copper sulfate, cobalt and zinc.
(**) mixture of 1-(4-amino-2-propyl-5-pyrimidinyl methyl)-2-picolium hydrochloride and methyl-4-acetamido-2-ethoxybenzoate (100:64)

EXAMPLE 3

400 broiler chickens (200 males and 200 females were equally divided into 4 groups (each group consisting of 100 chickens) and 2 ppm of multhiomycin with prescribed particle sizes was added to the feeds to be given to the respective groups except for the control group, to which ordinary commercial feed (produced by Zenno) were given and the feeding test was conducted by using such feeds for eight weeks according to a floor pen system.

Multhiomycin-blended feeds were prepared in the following way. That is, a wettable powder consisting of 20% of multhiomycin with various particle sizes, 40% of calcium carbonate, 30% of dextrose, 15% of kaolin and 5% of sorbitan monostearate was diluted in water and then spread to soybean meal to make a feed material containing 2% of multhiomycin, and then this was further blended with feedstuff so that multhiomycin was contained in an amount of 2 ppm therein.

It was found as a result that the smaller is the particle size of multhiomycin added, the higher is the degree of improvement.

TABLE 2

Change of average body weight and feed efficiency

| Group | Particle size of multhiomycin( ) | 0-week | 2-week | 4-week | 6-week | 8-week | Feed efficiency |
|---|---|---|---|---|---|---|---|
| Control | — | 42 | 236 | 689 | 1323 | 1812 | 2.44 |
| Added with multhiomycin | 52–44 | 42 | 227 | 695 | 1380 | 1891 | 2.34 |
| Added with multhiomycin | 43–37 | 42 | 242 | 705 | 1389 | 1902 | 2.32 |
| Added with multhiomycin | 3–5 | 42 | 252 | 733 | 1438 | 1975 | 2.21 |

(NOTES)
(1) Each numerical figure in the table is a mean value (gr.)
(2) Feed efficiency = total amount of feed ingested during the entire test period ÷ body weight gain during the entire test period.

Composition of basal feed:

| Feed materials | Used in 0 to 4-week period | Used in 5 to 8-week period |
|---|---|---|
| Corn | 49.5% | 52.0 |
| Soybean meal | 24.5 | 10.0 |
| Milo | 12.2 | 1.5 |
| Fats | — | 7.0 |
| Lucerne meal | 4.0 | 3.5 |
| Fish meal | 6.5 | 9.8 |
| Sodium chloride | 0.3 | 0.2 |
| Calcium carbonate | 1.5 | 1.5 |
| Calcium phosphate | 1.0 | 1.0 |
| Premix (*) | 0.5 | 0.5 |

Coccidium preventive (Amprolium plus) 125 ppm
(*) Premix contains vitamin A, vitamin $D_3$, vitamin E, vitamin $B_1$, vitamin $B_2$, vitamin $B_6$, vitamin $B_{12}$, pantothenic acid, nicotinic acid, choline chloride, folic acid, iron sulfate, copper sulfate, cobalt and zinc.

EXAMPLE 4

600 (180-days-old) egg-laying hens (white leghorns) were divided into three groups each consisting of 200 hens, and multhiomycin was added in an amount of 2 ppm and 10 ppm, respectively, to the feeds to be given to the respective groups except for the control group to which ordinary commercial feed for laying-hens was given, and the test was carried out by giving such feed to the respective groups continuously for six months. The test results are shown in Table 3 below. As apparent from the table, an eminent improvement in egg-laying was seen in the groups to which multhiomycin-blended feed was given.

TABLE 3

Change of average egg-laying rate (%)

| Group | 1st month from start of text | 2nd month | 3rd month | 4th month | 5th month | 6th month |
|---|---|---|---|---|---|---|
| Control | 74.2 | 80.5 | 81.2 | 82.1 | 82.0 | 82.5 |
| 2 ppm | 75.0 | 82.3 | 83.5 | 84.5 | 85.0 | 86.4 |
| 10 ppm | 74.8 | 82.9 | 85.4 | 85.6 | 85.7 | 87.1 |

EXAMPLE 5

40 weaned piglets (21 days old) were divided into four groups and commercially available piglet feed to which 0, 5, 10 and 20 ppm of multhiomycin was respectively added, was given to the respective groups continuously for four weeks, and the effects on body weight and feed efficiency were examined. As noted from Table 4 which shows the test results, the piglets bred with multhiomycin-added feed had 12.3 to 15.7% greater body weight than the piglets of the control group, and the feed efficiency was also improved by an amount of 0.32 to 0.37 over the control.

TABLE 4

| | Change of average body weight and feed efficiency | | | | | |
|---|---|---|---|---|---|---|
| Group | At start of test | 1 week later | 2 weeks later | 3 weeks later | 4 weeks later | Feed efficiency |
| Control | 4.43 | 6.44 | 8.55 | 11.21 | 13.45 | 2.02 |
| 5 ppm | 4.21 | 6.90 | 9.20 | 12.00 | 15.10 | 1.70 |
| 10 ppm | 4.50 | 6.52 | 9.44 | 12.44 | 15.35 | 1.68 |
| 20 ppm | 4.35 | 6.75 | 9.44 | 12.31 | 15.56 | 1.65 |

(NOTE)
Each numerical value in the table is a means value (kg).

EXAMPLE 6

80 (10-weeks-old) of first cross pigs (Landrace X Hampshire) were divided into four groups each consisting of 20 pigs (with same number of males and females) and multhiomycin was added in an amount of 5, 50 and 100 ppm, respectively to the feeds shown below, and the said feed were given to the respective groups except for the control group, and such feeds were given to the pigs of the respective groups continuously for 10 weeks. To the control group, an ordinary feed was given. The results are shown in Table 5 below. It was confirmed that, at the end of the test, the average body weight of the pigs given the multhiomycin-blended feeds was higher by 11.4 to 16.1% than that of the pigs of the control group, while the feed efficiency was also improved by 0.25 to 0.45 over the control.

TABLE 5

| | Change of average body weight and feed efficiency | | | | | |
|---|---|---|---|---|---|---|
| Group | At Start of test | 2 weeks later | 4 weeks later | 6 weeks later | 8 weeks later | 10 weeks later | Feed efficiency |
| Control | 21.3 | 26.0 | 35.2 | 43.2 | 50.3 | 60.4 | 3.66 |
| 5 ppm | 20.1 | 27.0 | 37.5 | 45.5 | 54.5 | 67.3 | 3.41 |
| 50 ppm | 20.9 | 27.5 | 38.0 | 47.8 | 56.2 | 69.4 | 3.38 |
| 100 ppm | 21.0 | 26.9 | 37.9 | 45.9 | 57.8 | 70.1 | 3.21 |

(NOTE)
Each numerical value in the table is a mean value (kg).

Composition of basal feed

| | | |
|---|---|---|
| | Corn | 48.9% |
| | Soybean meal | 13.0 |
| | Milo | 10.0 |
| | Defatted rice bran | 5.0 |
| | Barley | 8.0 |
| | Fish meal | 8.0 |
| | Lucerne meal | 4.0 |
| | Calcium carbonate | 1.4 |
| | Calcium phosphate | 0.7 |
| | Sodium chloride | 0.5 |
| | Premix (*) | 0.5 |

(*)Premix was the same as that used in Example 2.
NOTE:
Multhiomycin was added to the feeds in Examples 2,4,5, and 6 by spraying multhiomycin solution in acetone to the feed and removing acetone therefrom.

EXAMPLE 7

In a culture farm 100 Hamachis (Japanese name for young yellow tail, Soriola quinqueradiata) were cultured for 21 days using the feed containing 5 ppm of multhiomycin in which there were used as basic feed stuff "Feed Stuff for Fingerlings" prepared by Japan Haigoshiryo Co., Ltd.

After the test, various factors such as the body weight increase were measured and the number of surviving fish were counted.

The results obtained are shown in Table 6.

TABLE 6

| | Feed containing Multhiomycin | Control (only basic feed) |
|---|---|---|
| Number of initially stocked Hamachi | 100 | 100 |
| Initial average body weight (g) | 10.6 | 10.5 |
| Total weight of stocked fish (g) | 1,060 | 1,050 |
| Number of dead fish | 2 | 13 |
| Number of living fish | 98 | 87 |
| Final total weight of living fish (g) | 3,812 | 3,158 |
| Final average body weight of living fish (g) | 38.9 | 36.3 |
| Increase of total weight of living fish (g) | 2,752 | 2,108 |
| Total amount of feed supplied (g) | 18,438 | 17,920 |
| Increase factor of flesh | 6.7 | 8.5 |

As shown in Table 6, an increase of 7% in average body weight and of 31% in total body weight was obtained for the fish supplied with a feed containing multhiomycin over those of the control group supplied with feed containing no multhiomycin and significant improvement was obtained in the finally obtained yield as a result of the higher surviving ratio and rate of body weight increase.

EXAMPLE 8

In a culture farm 200 eels fingerlings (Angnilla japonica) were cultured for 70 days using a feed containing 10 ppm of multhiomycin in which there was used as basic feed stuff "Feed Stuff for Eel Fingerlings" prepared by Japan Haigoshiryo Co., Ltd.

After the test, various factors such as the body weight increase were measured and the number of surviving eels were counted. The results obtained are shown in Table 7.

TABLE 7

| | Feed containing Multhiomycin | Control (only basic feed stuff) |
|---|---|---|
| Number of initially stocked eels | 200 | 200 |
| Initial average body weight (g) | 1.30 | 1.31 |
| Total weight of stocked eels (g) | | |
| Number of dead eels | 0 | 14 |
| Number of living eels | 200 | 186 |
| Final total weight of living eels (g) | 1,530 | 1,207 |
| Final average body weight of living | 7.65 | 6.49 |

TABLE 7-continued

| | Feed containing Multhiomycin | Control (only basic feed stuff) |
|---|---|---|
| eels (g) | | |
| Increase of total weight of living eels (g) | 1,270 | 945 |
| Total amounts of feed supplied (g) | 1,549 | 1,531 |
| Increase factor of flesh | 1.22 | 1.62 |

As shown in Table 7, an increase of 18% in average body weight and of 27% of total body weight was obtained for the eel supplied with a feed containing multhiomycin over those of the control group supplied with feed containing no multhiomycin and significant improvement was obtained in the finally obtained yield as a result of the higher surviving ratio and rate of body weight increase.

EXAMPLE 9

5 parts of multhiomycin, 90 parts of ethylalcohol and 5 parts of sugar-ester were mixed throughly to form a solution. The solution can be used as a premix composition. The premix composition was mixed with feed or drink water in a predetermined amounts to form feed or drink water for animals, fishes and shellfishes.

EXAMPLE 10

10 parts of multhiomycin, 80 parts of sodium chloride, 3 parts of solbitanstearate and 7 parts of sugar ester were mixed throughly and grained to form powder for animals, fishes and shellfishes. The powder is mixed with feed or drinking water in a predetermined amounts to prepare feed or drinking water for animals, fishes and shellfishes.

EXAMPLE 11

1 part of multhiomycin, 5000 parts of starch, 4999 parts of kaolin were grained and mixed throughly to form powder.

The powder is given orally to animals as growth promoting agent in a suitable amount according to the growth state of the said animals.

EXAMPLE 12

5 parts of multhiomycin, 2500 parts of calcium carbonate, 2500 parts of glucose, 100 parts of sodium chloride, 4000 parts of kaolin, 400 parts of sodium bicarbonate, 200 parts of CMC, and 295 parts of sugar ester were grained and mixed throughly, and tablets were prepared using tablet machine. A suitable amounts of the tablets are orally given to animals as growth promoting agent.

EXAMPLE 13

1 part of multhiomycin, 300 parts of oil, 499 parts of water, 50 parts of sodium asparaginate and 100 parts of sugar ester were mixed throughly to form suspension. A suitable amount of the suspension are given orally to animals, fishes and shellfishes as growth promoting agent.

What we claim:

1. A method for promoting the growth of domestic animals which comprises administering to said animal a growth promoting effective amount of multhiomycin.

2. The method for promoting the growth according to claim 1, wherein said multhiomycin is administered to a domestic chicken, pig or cow.

3. The method for promoting the growth according to claim 1, wherein said multhiomycin is administered to a domestic chicken.

4. The method for promoting the growth according to claim 1, wherein said multhiomycin is administered to a domestic pig.

5. The method for promoting the growth according to claim 1, wherein said multhiomycin is administered to a domestic cow.

6. The method according to claim 1, wherein said multhiomycin is administered to said animal in an amount of 0.1 to 500 ppm admixed in the feed or drinking water for said animal.

* * * * *